US007718850B2

(12) United States Patent
Vancanneyt et al.

(10) Patent No.: US 7,718,850 B2
(45) Date of Patent: May 18, 2010

(54) METHODS AND MEANS FOR DELAYING SEED SHATTERING IN PLANTS

(75) Inventors: Guy Vancanneyt, Gentbrugge (BE); Martin Yanofsky, San Diego, CA (US); Sherry Kempin, San Diego, CA (US)

(73) Assignees: The Regents of the University of California, Oakland, CA (US); Bayer Bioscience N.V., Gent (BE)

( * ) Notice: Subject to any disclaimer, the term of this patent is extended or adjusted under 35 U.S.C. 154(b) by 0 days.

(21) Appl. No.: 10/561,793

(22) PCT Filed: Jun. 23, 2004

(86) PCT No.: PCT/EP2004/006888

§ 371 (c)(1),
(2), (4) Date: Jun. 9, 2006

(87) PCT Pub. No.: WO2004/113542

PCT Pub. Date: Dec. 29, 2004

(65) Prior Publication Data

US 2006/0248612 A1 Nov. 2, 2006

(30) Foreign Application Priority Data

Jun. 23, 2003 (EP) ................................ 03076952

(51) Int. Cl.
A01H 1/00 (2006.01)
C12N 15/82 (2006.01)
C12N 15/87 (2006.01)
C07H 21/04 (2006.01)
(52) U.S. Cl. ........................ 800/286; 800/285; 800/278; 536/24.5
(58) Field of Classification Search ........................ None
See application file for complete search history.

(56) References Cited

U.S. PATENT DOCUMENTS

| 6,420,628 B1 | 7/2002 | Ulvskov et al. | |
| 6,797,861 B2 | 9/2004 | Ulvskov et al. | |
| 6,998,517 B1 * | 2/2006 | Liljegren et al. | ............ 800/290 |
| 7,135,621 B2 * | 11/2006 | Yanofsky et al. | ............ 800/290 |

FOREIGN PATENT DOCUMENTS

| WO | WO 96/06932 | 3/1996 |
| WO | WO 97/13865 | 4/1997 |
| WO | WO 99/00502 | 1/1999 |
| WO | WO 99/00503 | 1/1999 |
| WO | WO 99/53050 | 10/1999 |
| WO | WO 00/04173 | 1/2000 |
| WO | WO 01/59122 | 8/2001 |
| WO | WO 01/79517 | 10/2001 |

OTHER PUBLICATIONS

Vancanneyt et al. 2002, Abstract, XIII Internation Conference on *Arabidopsis* Research, Sevilla, Spain Jun. 28-Jul. 2, 2002.*
Smith et al. 2000, Nature, 407:319-320.*
Thomas et al. 2001, The Plant Journal 25(4):417-425.*
Vancanneyt G. et al., "Podshatter resistance: exploitation of *Arabidopsis* genes to develop a productivity trait in oilseed ripe." XIII Int'l Conf. on *Arabidopsis* Res. (2002), No. 5-29, www.arabidopsis.org/news/events.jsp.
Rajani S. et al., "The *Arabidopsis* myc/bHLH gene *Alcatraz* enables cell separation in fruit dehiscence." Current Biol. (2001), vol. 11, pp. 1914-1922.
Liljegren S.J. et al., "*Shatterproof*MADS-box genes control seed dispersal in *Arabidopsis*" Nature (London), (2000), vol. 404, pp. 766-770.
Yu Hao. et al., "Agamous-Like 24, a dosage-dependent mediator of the flowering signals." PNAS (2002) vol. 99, No. 25, pp. 16336-16341.
Vancanneyt, et al., "Podshatter resistance: exploitation of *Arabidopsis* genes to develop a productivity trait in oilseed rape." XIII Int'l Conf. on *Arabidopsis* Res. (2002), No. 5-29 (poster).
Declaration Under 37 C.F.R. § 1.132 of Dr. Johan Botterman, Ph.D. in re Application of Liljegren and Yanofsky, dated (Oct. 8, 2002).
Amendment in re Application of Liljegren and Yanofsky, dated Oct. 8, 2002.
Bruce, et al., "Threshability of Shatter-Resistant Seed Pods in Oilseed Rape", Journal of Agricultural Engineering Research, vol. 80, No. 4, pp. 343-350 (2001).
Liljegren, et al., "Shatterproof MADS-Box Genes Control Seed Dispersal in *Arabidopsis*", Nature, vol. 404, pp. 766-770, (Apr. 13, 2000).
Luczkiewicz, Section I—continued: Genetics, Breeding and Biotechnology, Proceedings of the 7th International Rapeseed Congress vol. 2: 463-467 (May 11-14, 1987).
Prakash and Chopra, "Reconstruction of Allopolyploid Brassicas through Non-Homologous Recombination: Introgression of Resistance to Pod Shatter in Brassica Napus", Genetical Research Cambridge University Press, 56: pp. 1-2, (1990).
Ferrandiz, C., et al., "Negative Regulation of the Shatterproof Genes by Fruitfull During *Arabidopsis* Fruit Development", Science, vol. 289, pp. 436-438, Jul. 21, 2006.
Kadkol, G.P., et al., "Anatomical Basis of Shatter-Resistance in the Oilseed Brassicas", Australian Journal of Botany, vol. 34, pp. 595-601, (1986).
Petersen, M., et al., "Isolation and Characterization of a Pod Dehiscence Zone Specific Polygalacturonase From Brassica Napus", Plant Molecular Biology, vol. 31, pp. 517-527, (1996).

* cited by examiner

*Primary Examiner*—Anne Marie Grunberg
*Assistant Examiner*—Li Zheng
(74) *Attorney, Agent, or Firm*—Hunton & Williams LLP

(57) ABSTRACT

The invention relates to methods and compositions for modulating properties of fruit dehiscence in plants such Brassicaceae plants, specifically to improved methods and means for reducing seed shattering in Brassicaceae plants, particularly the Brassicaceae plants grown for oil production, to a degree which is agronomically important.

14 Claims, 1 Drawing Sheet

FIGURE 1.

```
IND1Atgene    1  ---atggaaaatggtatgtataaaaagaaaggagtgtgcgactcttgt--
IND Bngene1   1  gaattcgcccttcgcatgtataaaaagaagggtctatgcgtctctagtcc
IND Bngene2   1  gaattcgcccttggcatgtacaagaagaaaggtctatgcgtctctagtcc IND1Atgene   46  ---------------gtctcgtccaaaagcagatccaac---cacagccc
IND Bngene1  51  aaaaactctatat--gtctggttcaaaagcagatgcagcagccatagccc
IND Bngene2  51  aaaaactctatatatgtctggctcaaaagcagat---gcagccatagccc IND1Atgene   78  caaaagaagcatgatggagcctcagcctcaccatctcctcatggattgga
IND Bngene1  99  caatag--tcatgatgg------agcctcatcatctccttatgaactgga
IND Bngene2  98  caatag--tcatgatgg------agcatcatcatctccttatgaattgga IND1Atgene  128  acaaagctaatgatcttctcacacaagaacacgcagcttttctcaatgat
IND Bngene1 141  acaaacctattgatctcattacacaagaaaac---tcttttaaccacaat
IND Bngene2 140  acaaacctattgatctcattacagaagaaaac---tcttttaaccacaat IND1Atgene  178  cctcaccatctcatgttagatccacctcccgaaaccctaattcacttg--
IND Bngene1 188  cct---catttcatggtagatccaccttccgaaaccctaagccacttcca
IND Bngene2 187  cct---catttcatagtagatccaccttccgaaacccctaagccacttcca IND1Atgene  226  --------------------------------------------------
IND Bngene1 235  gcccccgccgacagtcttctccgatccggaggaggagagggaagcag---
IND Bngene2 234  gcccccgccgacaatcttctccggtcacggaggaggagaggaagcagcag IND1Atgene  226  --gacgaagacgaagagtacgatgaagacatggatgcgatgaaggagatg
IND Bngene1 282  ------aagacgaagaaggagaggaagagatagatgagatgaaggagatg
IND Bngene2 284  aagaagaagaagaagaaggagaggaagagatggatccgatgaagaagatg IND1Atgene  274  cagtacatgatcgccgtcatgcagcccgtagacatcgacctgccacggt
IND Bngene1 326  caatacgcgattgctgccatgcagcccgtagacatcgatccagccaccgt
IND Bngene2 334  caatacgcgattgctgccatgcagcccgtagacctcgatccagccaccgt IND1Atgene  324  ccctaagccgaaccgccgtaacgtaaggataagcgacgatcctcagacgg
IND Bngene1 376  tcctaagccgaaccgccgtaacgtaagggtaagcgaggaccccagacgg
IND Bngene2 384  tcctaagccgaaccgccgtaacgtaagggtaagcgacgaccctcagacgg IND1Atgene  374  tggttgctcgtcggcgtcgggaaaggatcagcgagaagatccgaattctc
IND Bngene1 426  tggtggctcgtcggcgtagagaaaggataagcgagaagatccggatattg
IND Bngene2 434  tggtggctcgtcggcgtagagaaaggataagcgagaagatccggatattg IND1Atgene  424  aagaggatcgtgcctggtggtgcgaagatggacacagcttccatgctcga
IND Bngene1 476  aagaggatggtgccaggcggtgcaaagatggacactgcctccatgcttga
IND Bngene2 484  aggaggatggtgccaggcggtgcaaagatggacactgcctccatgctcga IND1Atgene  474  cgaagccatacgttacaccaagttcttgaaacggcaggtgaggat----t
IND Bngene1 526  cgaagccatccgctacaccaagttcttgaaacggcaggtgaggct----t
IND Bngene2 534  cgaagccatccgctacaccaagttcttgaaacggcaggtgaggctagctt IND1Atgene  520  cttcagcctcactctcagattggagctcctatggctaaccctcttacct
IND Bngene1 572  cttcagcctcacactcagcttggggctcctatgtctgacccttctcgcct
IND Bngene2 584  cttcagcctcacactcagcttggagctcctatgtctgacccttcttgcct IND1Atgene  570  ttgttattaccacaactcccaaccctga
IND Bngene1 622  ttgttattaccacaactctcaa------
IND Bngene2 634  ttgttattatcataactcgcagccctg-
```

METHODS AND MEANS FOR DELAYING SEED SHATTERING IN PLANTS

CROSS-REFERENCE TO RELATED APPLICATIONS

This application is a U.S. national stage application of International Application No. PCT/EP2004/006888, filed on Jun. 23, 2004, which claims the benefit of European Patent Application No. 03076952.5, filed Jun. 23, 2003. All of the above applications are herein incorporated by reference in their entireties.

BACKGROUND OF THE INVENTION (i) Field of the Invention

The invention relates to plant genetic engineering. In particular, the invention relates to methods and compositions for modulating properties of fruit dehiscence in plants, particularly Brassicaceae plants, specifically to improved methods and means for reducing seed shattering, or reducing seed shattering until after harvest, in plants such as Brassicaceae plants, particularly the Brassicaceae plants grown for oil production, to a degree which is agronomically important.

(ii) Description of the Related Art

Siliques or pods from Brassicaceae plants release their seeds through a process called dehiscence. A silique consists of two carpels joined margin to margin. The suture between the margins forms a thick rib, called replum. As pod maturity approaches, the two valves separate progressively from the replum, along designated lines of weakness in the pod, eventually resulting in the shattering of the seeds that were attached to the replum. The dehiscence zone defines the exact location of the valve dissociation.

Shedding of seed (also referred to as "seed shatter" or "pod shatter") by mature pods, before or during crop harvest, is a universal phenomenon with crops that develop dry dehiscent fruits. Premature seed shatter results in a reduced seed recovery, which represents a problem in crops which are grown primarily for the seeds, such as oil producing Brassicaceae plants, particularly oilseed rape. Another problem related to premature seed shattering is an increase in volunteer growth in the subsequent crop year. In oilseed rape, pod-shatter related yield losses typically range from 10 to 25%, but can reach up to 50%, depending on the weather conditions.

Current commercial oilseed rape varieties are extremely susceptible to shattering. Kadkol et al. [(1986), Aust. J. Biol. 34: 79] reported increased resistance towards shattering in a single, Australian accession of rape. Variation in pod maturation has further been observed in mutants of rape stemming from irradiated seeds [Luczkiewicz (1987), Proc. 7th Int. Rapeseed Congress 2: 463]. However the traditional methods for breeding have been unsuccessful in introducing shatter resistance into rape cultivars, without interference in other desirable traits such as early flowering, maturity and blackleg resistance [Prakash and Chopra (1990), Genetical Research 56: 1].

Several genes, which promote or inhibit pod dehiscence have been identified in *Arabidopsis thaliana* through mutant analysis. These genes are encoding putative MADS box and basic helix-Loop-Helix mutants. Combined mutants in both SHATTERPROOF1 (SHP1; initially referred to as AGL1) and SHATTERPROOF2 (SHP2; initially referred to as AGL5) result in indehiscent siliques (i.e. siliques which remain closed upon maturity in *Arabidopsis thaliana*) (Liljegren et al., 2000, Nature 404, 766-770). Similarly, mutants in the INDEHISCENT gene in *Arabidopsis thaliana* (PCT publication WO 01/79517), as well as in ALCATRAZ (Rajani et al. 2001, Current Biology 11, 1914-1922) interfered with pod dehiscence leading to podshatter resistance. Constitutive expression of FRUITFUL (FUL), a repressor of SHP and IND, in *Arabidopsis thaliana* also resulted in indehiscent siliques (Ferrandiz et al., 2000, Science, 289, 436-438). These transcription factors are thus regulating the development of the valves, including the valve margins and the dehiscence zone.

Genes for a number of hydrolytic enzymes, such as endopolygalacturonases, which play a role, during pod dehiscence, in the programmed breakdown of the dehiscence zone in pods from Brassicaceae plants have also been identified (see e.g. WO 97/13865; Petersen et al., Plant. Mol. Biol., 1996, 31:517-527).

To isolate mutant alleles corresponding to ind, alc or shp1-shp2 in economically important Brassicaceae plants, such as oilseed rape, is a laborious and time consuming task. Moreover, such isolation may be complicated by the amphidiploidy in oilseed rape and the consequent functional redundancy of the corresponding genes.

It has been described that the expression of the ALC, IND, AGL1 and AGL5 genes or their homologues, may be downregulated using gene silencing techniques such as antisense suppression or cosuppression (WO99/00503; WO01/79517; WO0159122).

Vancanneyt et al., 2002 (XIII International Conference on *Arabidopsis* Research, Sevilla, Spain June 28-Jul. 2; 2002) reported that the expression of FUL from *A. thaliana* under control of a CaMV 35S promoter in oilseed rape, resulted in a number of podshatter resistant transformants. Pods of such podshatter resistant lines had no dehiscence zone, and opening of the pods could only be achieved by random fracture of the valves by applying considerable pressure.

Vancanneyt et al., 2002 (XIII International Conference on *Arabidopsis Research, Sevilla, Spain June* 28-Jul. 2; 2002) also reported that silencing of the IND gene in *Arabidopsis thaliana* using so-called dsRNA silencing techniques resulted in almost complete podshatter resistance. 98% of the transgenic *Arabidopsis* lines developed siliques, which did not open along the valve suture, and could only be opened by applying considerable pressure to the valves.

Furthermore, experiments described in this application (see below) indicate that silencing of the IND gene in *Brassica napus* using dsRNA gene silencing techniques, whereby the dsRNA sequence is identical to one of the IND homologues of *Brassica napus*, results in podshatter resistant lines with pods that bearly open by random fracture of the valves in a standardized random impact test.

It is important to realize that while seed shattering constitutes an important problem in oilseed rape culture, which may be solved by developing podshatter resistant lines, ultimately, separation of the seeds from the pods is still required. In normal agricultural practice this is achieved by threshing of the pods by a combine harvester. Threshing of the pods by a combine harvester must be complete and must cause minimum damage to the seeds thus released. However, as pod strength increases, the more severe action required to thresh them causes an unacceptable level of damage to the seed. The pods of podshatter resistant Brassicaceae plants should thus not be so strong that they cannot be threshed in a combine harvester (Bruce et al. 2001, J. Agric. Engng Res. 80, 343-350).

The art thus remains defective in providing method and means for reducing seed shattering in Brassicaceae plants, particularly in oilseed rape, while retaining a sufficient threshability.

These and other objects are achieved by the present invention, as indicated by the various embodiments described in the summary of the invention, detailed description and claims.

SUMMARY AND OBJECTS OF THE INVENTION

In one embodiment of the invention, a method is provided for reducing seed shattering in a plant, preferably a Brassicaceae plant, such as an oilseed rape plant, comprising the steps of:

creating a population of transgenic lines of the plant, preferably the Brassicaceae plant, wherein the transgenic lines of the population exhibit variation in podshatter resistance, and wherein the population is obtainable by introducing a chimeric gene into cells of the plant, preferably the Brassicaceae plant, to create transgenic cells, the chimeric gene comprising the following operably linked DNA fragments:
  a plant-expressible promoter;
  a DNA region which when transcribed yields a double-stranded RNA molecule capable of reducing the expression of a gene endogenous to the plant, preferably the Brassicaceae plant, the gene being involved in the development of a dehiscence zone and valve margin of a pod of the plant, preferably the Brassicaceae plant, such as a gene selected from the group of INDEHISCENT gene from *Arabidopsis thaliana*, ALCATRAZ gene from *Arabidopsis thaliana*, SHATTERPROOF1 gene from *Arabidopsis thaliana*, SHATTERPROOF2 gene from *Arabidopsis thaliana* or a homologous gene thereof present in the Brassicaceae plant, and the RNA molecule comprising a first and second RNA region wherein
    (i) the first RNA region comprises a nucleotide sequence of at least 19 consecutive nucleotides having about 94% sequence identity to the nucleotide sequence of the endogenous gene involved in the development of a dehiscence zone and valve margin of the pod;
    (ii) the second RNA region comprises a nucleotide sequence complementary to the 19 consecutive nucleotides of the first RNA region;
    (iii) the first and second RNA region are capable of base-pairing to form a double stranded RNA molecule between at least the 19 consecutive nucleotides of the first and second region;
  (b) a 3' end region comprising transcription termination and polyadenylation signals functioning in cells of the plant;

wherein the chimeric gene, when expressed in cells of the plant, preferably the Brassicaceae plant increases podshatter resistance compared to podshatter resistance in an untransformed plant, preferably an untransformed Brassicaceae plant, while maintaining an agronomically relevant threshability of the pods of the plant;

regenerating transgenic lines from the transgenic cells; and
selecting a podshatter resistant plant from the population wherein the plant has pods exhibiting delayed seed shattering.

Agronomically relevant threshability preferably corresponds to a half-life time of the pods in a Random Impact test between 10 and 60 seconds, preferably between 40 and 60 seconds.

In an embodiment of the invention, the plant expressible promoter may be a relatively weak plant expressible promoter such as an opine synthetase promoter from *Agrobacterium* spp., a promoter selected from a nopaline synthetase promoter, an octopine synthetase promoter, a agrocinopine synthetase promoter or a mannopine synthetase promoter, or a dehiscence zone or valve margin selective promoter and the sense and antisense RNA region may comprises a nucleotide sequence of about 19 to about 500 consecutive nucleotides having a sequence similarity of about 90% to about 100% to the nucleotide sequence of the endogenous gene.

In another embodiment of the invention the first RNA region may comprise a sequence of about 50 to about 500 consecutive nucleotides having about 50% to about 88%, preferably about 65% to about 75% sequence identity with the endogenous gene; the second RNA may comprise a nucleotide sequence having about 90 to about 100% sequence similarity to the complement of the nucleotide sequence of the first RNA region; and the first and second RNA region are capable of forming a double stranded RNA region.

In yet another embodiment of the invention, the Brassicaceae plant may be an oilseed rape plant; the first RNA region may comprise a nucleotide sequence comprising at least 19 consecutive nucleotides from the nucleotide sequence of a second gene involved in the development of a dehiscence zone and valve margin of a pod, the second gene being endogenous to a Brassicaceae plant different from oilseed rape such as is a gene selected from the group of INDEHISCENT gene from *Arabidopsis thaliana*, ALCATRAZ gene from *Arabidopsis thaliana*, SHATTERPROOF1 gene from *Arabidopsis thaliana*, SHATTERPROOF2 gene from *Arabidopsis thaliana*; the second RNA comprises a nucleotide sequence having about 90 to about 100% sequence similarity to the complement of the nucleotide sequence of the first RNA region; and the first and second RNA region are capable of forming a double stranded RNA region.

In another embodiment of the invention, a method is provided for reducing seed shattering in an oilseed rape plant comprising the following steps:
  (2) creating a population of transgenic lines of the oilseed rape plant, wherein the transgenic lines of the population exhibit variation in podshatter resistance, and wherein the population is obtainable by
    (i) introducing a chimeric gene into cells of the oilseed rape plant, to create transgenic cells, the chimeric gene comprising the following operably linked DNA:
      (a) a plant-expressible promoter;
      (b) a DNA region which when transcribed yields a double-stranded RNA molecule capable of reducing the expression of a gene endogenous to the oilseed rape plant, the gene being involved in the development of a dehiscence zone and valve margin of a pod of the oilseed rape plant, such as a gene selected from the group of INDEHISCENT gene from *Arabidopsis thaliana*, ALCATRAZ gene from *Arabidopsis thaliana*, SHATTERPROOF1 gene from *Arabidopsis thaliana*, SHATTERPROOF2 gene from *Arabidopsis thaliana*, and the RNA molecule comprising a first and second RNA region wherein
        (i) the first RNA region comprises a nucleotide sequence of at least 50 consecutive nucleotides having at least about 90% sequence identity to the nucleotide sequence of a gene from *Arabidopsis thaliana* involved in the development of a dehiscence zone and valve margin of the pod;

(ii) the second RNA region comprises a nucleotide sequence complementary to the 50 consecutive nucleotides of the first RNA region;

(iii) the first and second RNA region are capable of base-pairing to form a double stranded RNA molecule between at least the 50 consecutive nucleotides of the first and second region;

(c) a 3' end region comprising transcription termination and polyadenylation signals functioning in cells of the plant;

(ii) regenerating transgenic lines from the transgenic cells; and (3) selecting a podshatter resistant plant from the population wherein the plant has pods exhibiting reduced seed shattering.

The invention also relates to the chimeric genes according to the invention, as well as cells of a Brassicaceae plant and their seeds and progeny comprising such chimeric genes, and Brassicaceae plants obtainable by the methods according to the invention.

It is yet another object of the invention to provide isolated DNA fragments comprising a nucleotide sequence from SEQ ID No 2 or SEQ ID No 3 and isolated DNA fragments obtainable from a Brassicaceae plant, which hybridizes under stringent conditions to a DNA fragment comprising the nucleotide sequence of SEQ ID No 2 or No 3. The invention also relates to the use of such an isolated DNA fragment to reduce seed shatter or increase pod shatter resistance in Brassicaceae plants such as oilseed rape.

The invention also provides an agricultural method comprising the steps of (i) sowing seeds according to the invention or planting plants according to the invention in a field;

(ii) growing the plants until the pods are mature;

(iii) harvesting seeds from the pods by threshing in a combine harvester.

BRIEF DESCRIPTION OF THE FIGURES

FIG. 1: alignment of the 5' end of the open reading frames from AT-IND (SEQ ID NO:1); BN1-IND (SEQ ID NO:2) and BN2-IND (SEQ ID NO:3).

DETAILED DESCRIPTION OF PREFERRED EMBODIMENTS

The invention is based on the unexpected observation that moderate dsRNA gene silencing of genes involved in the development of the dehiscence zone and valve margins of pods in Brassicaceae plants, particularly oilseed rape plants, allows the isolation of transgenic lines with increased pod shatter resistance and reduced seed shattering, the pods of which however may still be opened along the dehiscence zone by applying limited physical forces. This contrasts with transgenic Brassicaceae plants, wherein the dsRNA silencing is more pronounced, such as the ones described in the art, which result in transgenic lines with indehiscent pods, which no longer can be opened along the dehiscence zone, and which only open after applying significant physical forces by random breakage of the pods, whereby the seeds remain predominantly within the remains of the pods.

Moderate dsRNA gene silencing of genes can be conveniently achieved by e.g. operably linking the dsRNA coding DNA region to a relatively weak promoter region, or by e.g. choosing the sequence identity between the complementary sense and antisense part of the dsRNA encoding DNA region to be lower than 90% and preferably within a range of about 60% to 80%.

Without intending to limit the invention to a particular mode of action, it is thought that the silencing of the expression level of the endogenous genes involved in dehiscence zone and valve margin development in these instances is incomplete, such that the expression of the endogenous gene in the presence of the gene-silencing chimeric genes according to the invention is about 5% to about 20%, particularly about 10% of the expression of the endogenous gene in the absence of the gene-silencing chimeric genes according to the invention.

Thus, in one embodiment of the invention, a method is provided for reducing seed shattering in a Brassicaceae plant by creation of a population of transgenic lines of a Brassicaceae plant, wherein said transgenic lines of said population exhibit variation in podshatter resistance. This population may be obtained by introducing a chimeric gene into cells of a Brassicaceae plant, to create transgenic cells, whereby the chimeric gene comprises a plant-expressible promoter and a 3' end region comprising transcription termination and polyadenylation signals functioning in cells of a Brassicaceae plant, operably linked to a DNA region which when transcribed yields a double-stranded RNA molecule capable of reducing the expression of a gene endogenous to a Brassicaceae plant, involved in the development of a dehiscence zone and valve margin of a pod of said Brassicaceae plant. The RNA molecule comprises a first (sense) RNA region and second (antisense) RNA region whereby the first RNA region comprises a nucleotide sequence of at least 19 consecutive nucleotides having about 94% sequence identity to the nucleotide sequence of the endogenous gene;

the second RNA region comprises a nucleotide sequence complementary to the at least 19 consecutive nucleotides of the first RNA region;

the first and second RNA region are capable of base-pairing to form a double stranded RNA molecule between the mentioned at least 19 consecutive nucleotides of the first and second region.

Expression of the chimeric gene in Brassicaceae plants increases podshatter resistance compared to podshatter resistance in an untransformed Brassicaceae plant, while however maintaining an agronomically relevant threshability of the pods. After regeneration of transgenic lines from the transgenic cells comprising the chimeric genes according to the invention, a podshatter resistant plant can be selected from the generated population.

As used herein, a gene <<involved in development of a dehiscence zone and valve margins of a pod>> refers to a gene, which when mutated in a plant, leads to the development of pods wherein the dehiscence zone and/or the suture of the pod is less or not developed, either alone, or in combination with mutations in other such genes. These genes include the INDEHISCENT gene from *Arabidopsis thaliana*, the ALCATRAZ gene from *Arabidopsis thaliana*, the SHATTERPROOF1 gene from *Arabidopsis thaliana* or the SHATTERPROOF2 gene from *Arabidopsis thaliana* or a homologous gene thereof. These genes encode proteins comprising MADS box or basic Helix-Loop-Helix domains and are believed to be transcriptional activators.

Nucleotide sequences of these genes or parts thereof can be found in databases and have the following accession numbers: AT-SHP1 (M55553; AV557878; AV556852); AT-SHP2 (M55550; BG459390): AT-IND (AX320925); a homologue of AT-IND from *Brassica rapa* subsp. *pekinenis* (AT002234);

AT-ALC (AX211753; AX211755; AX211760). All these nucleotide sequences are hereby incorporated specifically by reference.

DNA fragments comprising variant sequences of the above mentioned nucleotide sequences can be isolated from other Brassicaceae plants, particularly from other oilseed rape plants, subspecies or varieties by methods commonly known in the other.

These methods include hybridization under stringent conditions of genomic or cDNA libraries derived from such other plants, subspecies or varieties with a probe consisting of part or all of any of the above mentioned genes.

Such variants of genes involved in dehiscence zone and valve margin development or suitable parts thereof may also be identified and isolated using e.g. polymerase chain reaction amplification using an appropriate pair of oligonucleotides having at least about 16 contiguous nucleotides, particularly at least about 50 contiguous nucleotides, more particularly at least about 100 contiguous nucleotides of the nucleotide sequence of the above mentioned genes involved in dehiscence zone and valve margin development. Preferably, the sequence of the oligonucleotides is derived from parts of the nucleotide sequence of the genes involved in development of dehiscence zone and valve margins of pods of Brassicaceae plants, which are different from those parts of these genes encoding common protein motives such as MADS boxes or K-regions or basic helix-loop-helix regions. Examples of PCR amplified sequences of genes involved in the development of dehiscence zone and valve margins of pods of Brassicaceae plants are DNA molecules having the sequence of SEQ ID NO 2 or SEQ ID No 3. Examples of nucleotide sequences of suitable oligonucleotides primers to amplify parts of genes involved in the development of dehiscence zone and valve margins of pods of Brassicaceae plants are represented in SEQ ID No 4 to SEQ ID No 8.

"Stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

As used herein, "a gene endogenous to a Brassicaceae plant" is a gene that naturally occurs in the species of the Brassicaceae family that has been chosen for modulation of the pod shatter resistance.

As used herein, <<an agronomically relevant threshability>> refers to the resistance of a pod, particularly an oilseed rape pod, to opening along the dehiscence zone of the pod with concurrent release of the seeds, upon application of physical forces that allow complete opening of the pods while preventing damage to the seeds, as they are used e.g. in a combine harvester. A good correlation has been found between the half-life time of pods in a random impact test and their threshability. Random impact tests (RITs) and algorithms to define the half-life time of pods in such RITs have been described in Bruce et al., 2001 (J. Agric. Engng Res. 80, 343-350) and Morgan et al., 1988 (Fields Crop Research 58, 153-165). Both publications are hereby incorporated by reference. Briefly, a sample of immature pods is placed in a closed drum together with steel balls, and the drum is then vigorously agitated for increasing periods of times (e.g. 5 s, 10 s, 20 s, 40 s). After each period, the drum is opened and the number of broken and damaged pods is counted. The most accurate estimation of the level of shattering resistance for each line is calculated by fitting a linear x linear curve to all the available data and estimating the time take for half of the pods within a sample to be broken ("pod shatter half life"). It is important however that pods open mainly along the dehiscence zone, and are not simply pulverized, as may occur with indehiscent pods. Pod shatter half lives of oilseed rape, as determined in a RIT, which correspond to agronomically relevant threshability should not exceed 60 seconds. Typical values for control lines of commercially available oilseed rape varieties are about 10 seconds. Thus, lines with improved pod shatter resistance with agronomically relevant threshability have a pod shatter half life in RIT between about 10 and about 60 seconds, preferably between about 20 and about 60 seconds, particularly between about 40 and about 60 seconds.

In a particular embodiment of the methods of the invention, the moderate gene silencing can be achieved by employing a relatively weak plant expressible promoter.

As used herein, the term "promoter" denotes any DNA which is recognized and bound (directly and indirectly) by a DNA-dependent RNA-polymerase during initiation of transcription. A promoter includes the transcription initiation site, and binding sites for transcription initiation factors and RNA polymerase, and can comprise various other sites (e.g. enhancers), at which gene expression regulatory proteins may bind.

The term "regulatory region", as used herein, means any DNA, that is involved in driving transcription and controlling (i.e. regulating) the timing and level of transcription of a given DNA sequence, such as a DNA coding for a protein or polypeptide. For example, a 5' regulatory region (or "promoter region") is a dNA sequence located upstream (I.e. 5') of a coding sequence and which comprises the promoter and the 5'-untranslated leader sequence. A 3' regulatory region is a DNA sequence located downstream (i.e. 3') of the coding sequence and comprises suitable transcription termination and or regulation signals, including one or more polyadenylation signals.

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e. certain promoters of viral or bacterial origin such as the CaMV35S promoter (Hapster et al. 1988, Mol. Gen. Genet. 212, 182-190), the subterranean clover virus promoter No 4 or No 7 (WO9606932) or T-DNA gene promoters.

As used herein "a relatively weak plant expressible promoter" is a promoter which initiates and controls transcription of the operably linked DNA fragments about 10 to about 100 times less efficient that an optimal CaMV35S promoter. Relatively weak plant expressible promoters include the promoters or promoter regions from the opine synthase genes of *Agrobacterium* spp. such as the promoter or promoter region of the nopaline synthase, the promoter or promoter region of the octopine synthase, the promoter or promoter region of the mannopine synthase, the promoter or promoter region of the agropine synthase and any plant expressible promoter with comparably activity in transcription initation. Other relatively weak plant expressible promoters may be dehiscence zone selective promoters, or promoters expressed predominantly or selectively in dehiscence zone and/or valve margins of Brassicaceae pods, particularly oilseed rape pods, such as the promoters described in WO97/13865.

In this embodiment of the invention, the chimeric gene may comprise a transcribed DNA region encoding a dsRNA, wherein the sense and antisense RNA regions comprise a nucleotide sequence which has a high degree of sequence identity with the endogenous gene (or its complement) of the Brassicaceae plant, the pods of which are to rendered more resistant. Thus, sense and antisense RNA regions may comprise at least about 50, 100, 200, 500 or more consecutive nucleotides having about 90% to about 100% sequence identity to the endogenous gene of the Brassicaceae plant or its complement.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other is regarded as a position with non-identical residues. The alignment of the two sequences is performed by the Needleman and Wunsch algorithm (Needleman and Wunsch 1970) Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

In another embodiment of the invention, the moderate gene silencing can be achieved by employing a first and second RNA region that have a sequence identity to an endogenous gene involved in dehiscence zone and valve margin development of the pod, or part thereof, or their complementary sequences, ranging between about 60 to about 88% sequence identity, preferably ranging between about 60 to about 75% sequence identity. The length of the sense and antisense RNA regions may be at least 50, 100, 200, 500 or more nucleotides.

It has been observed by alignment of the sense RNA region (or complement of the antisense region) of the *Arabidopsis thaliana* derived sequence of IND used in the chimeric genes of the Examples and the corresponding region of the nucleotide sequences of the *Brassica napus* IND genes that there is not a single subregion of 21 consecutive nucleotides which are either identical or have only one mismatch between each of the *Brassica napus* sequences and the *Arabidopsis thaliana* sequence (see FIG. 2). The sequences share however several subsequences of 19 consecutive nucleotides with only one mismatch (i.e. having a sequence identity of about 94%). Although not intending to limit the invention to a particular mode of action, it is thought that the absence of nucleotide sequence "words" of 21 nucleotides shared between the dsRNA molecule and the endogenous gene may play an important role in the moderation of the gene silencing, as these 21-mers are generally expected to play an important role in the initiation and maintenance of dsRNA mediated post-transcriptional silencing.

For oilseed rape plants, a moderate gene-silencing response can be conveniently achieved by using a chimeric gene encoding a dsRNA molecule, wherein the sense and antisense region comprise a nucleotide sequence having about 90% or 95% sequence identity, particularly are identical to a nucleotide sequence of at least 19 consecutive nucleotides from a gene involved in dehiscence zone and valve margin development of the silique from *Arabidopsis thaliana*. The nucleotide sequence may however be longer than 19 nucleotides and may be 50, 100, 200, 500 or even more nucleotides in length.

In a particular embodiment of the invention, reduced seed shattering in oilseed rape can be achieved by using a chimeric gene encoding a dsRNA molecule wherein the sense and antisense regions correspond to the nucleotide sequence of the IND gene of *Arabidopsis thaliana* (SEQ ID No 1) from nucleotide +12 to +223 relative to the ATG startcodon of the *Arabidopsis thaliana* IND gene or its complement, i.e. from the nucleotide at position 27 to the nucleotide at position 237 in SEQ ID No 1.

dsRNA encoding chimeric genes according to the invention may comprise a heterologous intron located in the spacer sequence between the sense and antisense RNA regions in accordance with the disclosure of WO 99/53050 (incorporated herein by reference).

The invention also provides novel isolated DNA fragments comprising the nucleotide sequence of SEQ ID No 20R SEQ ID No 3. and the use thereof for modulating or increasing podshatter resistance in plants, such as Brassicaceae plants, particularly oilseed rape plants.

Preferred Brassicaceae to be treated in accordance with this invention, besides *Brassica napus*, include *Brassica juncea, Brassica oleraceae, Brassica carinata, Brassica nigra, Brassica campestris* and the like, and any intergenic crosses or synthetic varieties thereof. Other Brassicaceae, which may be treated according to the methods of the inventions include *Brassica cretica* (mustard), *Brassica elongata* (elongated mustard), *Brassica narinosa* (broadbeaked mustard), *Brassica nigra* (black mustard), *Brassica rapa* (field mustard), *Brassica rupstris* (mustard), *Brassica tournefortii* (Asian mustard). *Brassica napus* (2n=38, genome AACC) is an amphidiploid species, which originated from a spontaneous hybridization of *Brassica rapa* L. (syn. *B. campestris;* 2n=20, AA) and *Brassica oleracea* L. (2n=18, CC). *B. napus* contains the complete chromosome sets of these two diploid genomes.

As used herein, <<a plant from the family Brassicaceae>> or <<a Brassicaceae plant>> is a plant which according to the current botanical standard would be classified into the family Brassicaceae (formerly Cruciferaeae). Brassicaceae (Mustard) family members are easy to distinguish. They are annual or perannual plants with alternate leaves without stipules and posses simple inflorescence or branched racemes. The flowers are bilaterally symmetrical and hypogynous. With few exceptions, the flowers have 4 petals (free) alternating with 4 sepals (free); 6 stamens (4 long and 2 short), an ovary of 2 united carpels with parital placenta, 2 locular through the formation of a membranous false septum; fruit is a dehiscent capsule opening by 2 valves. Brassicaceae include inter alia the following genera: *Sisymbrium, Descurania, Alliaria, Arabidopsis, Myagrum, Isatis, Bunia, Erysium, Hesperis, Malcolmia, Matthiola, Chorispora, Euclidium, Barbarea, Rorippa, Armoracia, Nasturtium, Dentaria, Cardamine, Cardaminopsis, Arabis, Lunaria, Alyssum, Berteroa, Lobularia, Draba, Erophila, Cochlearia, Camelina, Neslia, Capsella, Hornungia, Thlsapi, Iberis, Lepidium, Cardaria, Coronopus, Subularia, Conringia, Diplotaxis, Brassica, Sinapsis, Eruca, Erucastrum, Coincya, Hirschfeldia, Cakile, Rapistum, Crambe, Enarthrocarpus, Rhaphanus* and *Clausia*.

<<Oilseed rape>> as used herein, should be understood to include the species *Brassica napus, Brassica junceae* and *Brassica campestris*.

The means and methods of the invention may also be used in plants other than Brassicaceae, specifically plants which have fruits or pods wherein valves have to separate to release the seeds. These include members of the family Fabaceae, such as pea, beans, soybean and the like.

It is also an object of the invention to provide plant cells and plants containing the chimeric genes or the RNA molecules according to the invention. Gametes, seeds (including crushed seeds and seed cakes), embryos, either zygotic or somatic, progeny or hybrids of plants comprising the chimeric genes of the present invention, which are produced by traditional breeding methods are also included within the scope of the present invention.

The plants obtained by the methods described herein may be further crossed by traditional breeding techniques with other plants to obtain podshatter resistant progeny plants comprising the chimeric genes of the present invention.

The following non-limiting Examples describe the construction of chimeric genes for reducing seed shattering or modulating fruit dehiscence in Brassicaceae plants, and Brassicaceae plants comprising such chimeric genes, exhibiting reduced seed shattering in agronomically relevant ranges.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:

SEQ ID No. 1: nucleotide sequence of the INDEHISCENT gene of *A. thaliana* (AT-IND)

SEQ ID No. 2: nucleotide sequence of a INDEHISCENT homologue from *Brassica napus* (BN1-IND)

SEQ ID No. 3: nucleotide sequence of a second INDEHISCENT homologue from *Brassica napus* (BN2-IND)

SEQ ID No. 4: common nucleotide sequence of oligonucleotides CO109/CO111

SEQ ID No. 5: common nucleotide sequence of oligonucleotides CO110/CO112

SEQ ID No. 6: common nucleotide sequence of oligonucleotides CO113/CO114

SEQ ID No. 7: common nucleotide sequence of oligonucleotides CO115/CO117

SEQ ID No. 8: common nucleotide sequence of oligonucleotides CO116/CO118

SEQ ID No. 9: nucleotide sequence of the SHATTERPROOF 1 gene of *A. thaliana* (AT-SHP1)

SEQ ID No. 10: nucleotide sequence of the SHATTERPROOF 2 gene of *A. thaliana* (AT-SHP2)

SEQ ID No. 11: nucleotide sequence of the ALCATRAZ gene of *A. thaliana* (AT-ALC)

EXAMPLES

Example 1

Construction of Chimeric Genes Encoding dsRNA Capable of Reducing the Expression of a Gene Involved in Dehiscence Zone and Valve Margin Development and Introduction into Plants Based on IND Gene Sequences A 5' end fragment of the IND gene of *Arabidopsis thaliana* or of the homologous genes from *Brassica napus* was amplified by PCR under standard conditions, using as template genomic DNA from *Arabidopsis thaliana* or PCR amplified DNA from *B. napus* comprising the sequences of SEQ ID No 2 or SEQ ID No 3 and the following oligonucleotides:

For the 5' end of the At-IND gene: an oligonucleotide comprising the sequence of SEQ ID No 7 and an oligonucleotide comprising the sequence of SEQ ID No 8, equipped with appropriate restriction enzyme sites at the 5' end of the oligonucleotides to allow directional cloning.

For the 5' end of the BN1-IND gene: an oligonucleotide comprising the sequence of SEQ ID No 4 and an oligonucleotide comprising the sequence of SEQ ID No 6, equipped with appropriate restriction enzyme sites at the 5' end of the oligonucleotides to allow directional cloning.

For the 5' end of the BN2-IND gene: an oligonucleotide comprising the sequence of SEQ ID No 4 and an oligonucleotide comprising the sequence of SEQ ID No 5, equipped with appropriate restriction enzyme sites at the 5' end of the oligonucleotides to allow directional cloning.

The amplified PCR fragments of the homologous genes from *B. napus* have about 90% sequence identity, whereas the sequence identity between the At-Ind gene and each of the BN-Ind genes is about 65% (see FIG. 1).

Using standard cloning techniques the following chimeric genes encoding dsRNA capable of reducing the expression of a gene involved in dehiscence zone and valve margin development of a pod have been constructed and introduced into T-DNA vectors, together with an appropriate selective marker gene (plant-expressible bar gene).

pTCO219 pTCO219 is a T-DNA vector comprising between the T-DNA borders

1. A dsRNA encoding chimeric gene (p35S-dsRNA/AtIND) comprising the following operably linked DNA fragments:

p35S: Promoter region from the Cauliflower Mosaic Virus 35S (Odell et al. (1985) Nature 313: 810-812)

AtIND$^{sense}$: A 211 by fragment from nucleotide +12 to +223 relative to the ATG startcodon of the *Arabidopsis thaliana* Ind1 gene, encoding a Basic Helix Loop Helix protein involved in pod dehiscence (corresponding to the nucleotide sequence of SEQ ID No 1 from the nucleotide at position 27 to the nucleotide at position 239). This fragment is cloned in sense orientation.

Pdk-intron: Sequence of the second intron from the pyruvate orthophosphate dikinase gene (termed pdk gene)

from Flayeria trinervia (Rosche & Westhoff (1995) Plant Molecular Biology 29-4: 663-678)

AtIND$^{antisense}$: A 211 by fragment from nucleotide +12 to +223 relative to the ATG startcodon of the *Arabidopsis thaliana* Ind1 gene, encoding a Basic Helix Loop Helix protein involved in pod dehiscence (corresponding to the nucleotide sequence of SEQ ID No 1 from the nucleotide at position 27 to the nucleotide at position 239). This fragment is cloned in antisense orientation.

3'ocs: the 3' untranslated end from the octopine synthase gene (De Greve et al. (1982) J. Mol. Appl. Genet. 1: 499-512; Gielen et al. (1984) EMBO J. 3: 835-846).

2. A chimeric bar gene comprising the following operably linked DNA fragments:

pSSuAra: a 1726 bp DNA fragment of promoter and leader sequence from the *Arabidopsis thaliana* rbcS ATS1A gene (Krebbers et al., 1988, Plant Mol. Biol. 11: 745-759).

bar: the coding sequence of the bialaphos resistance gene from *Streptomyces hygroscopicus* (Thompson et al., 1987, EMBO 6, 2519).

3'g7: A 211 bp DNA fragment containing the 3' end formation signals obtained from the 3' untranslated region of the TL-DNA gene 7 on pTiB6S3 (Dhaese et al., 1983, EMBO 2: 419; Velten and Schell, 1985, Nucl. Acids Res. 13: 6981).

Plasmid pTCO219 is derived from pGSV1. The basic intermediate vector pGSV1 has essentially been derived from pGSC1700 (Cornelissen and Vandewiele, 1989) and comprises the following structural elements:

the plasmid core comprising the origin of replication from the plasmid pBR322 (Bolivar et al., 1977) for replication in *Escherichia coli* (pBRori) and a restriction fragment comprising the origin of replication from the *Pseudomonas* plasmid pVS1 (Itoh et al., 1984) for replication in *Agrobacterium tumefaciens* (pVSlori);

a selectable marker gene conferring resistance to streptomycin and spectinomycin (Sm/Sp) for propagation and selection of the plasmid in *Escherichia coli* and *Agrobacterium tumefaciens*;

An artificial T-region consisting of the left and right border sequences of the TL-DNA from pTiB6S3 and polylinker allowing the insertion of GOI between the T-DNA border.

pTKC89 pTKC89 a is a T-DNA vector, similar to pTCO219, wherein the CaMV35S promoter has been exchanged for a nopaline synthase promoter from *Agrobacterium tumefaciens*, through standard cloning techniques.

pTCO212 pTCO212 is a T-DNA vector comprising between the T-DNA borders

1. A dsRNA encoding chimeric gene (p35S-dsRNA/BN2-IND) comprising the following operably linked DNA fragments:

p35S: Promoter region from the Cauliflower Mosaic Virus 35S (Odell et al. (1985) Nature 313: 810-812).

BN2-IND$^{sense}$: A 261 by fragment from nucleotide +12 to +273 relative to the ATG startcodon of a *Brassica napus* homolog (homolog 2) of the *Arabidopsis thaliana* Ind1 gene, encoding a Basic Helix Loop Helix protein involved in pod dehiscence (corresponding to the nucleotide sequence of SEQ ID No 3 from the nucleotide at position 30 to the nucleotide at position 290). This fragment is cloned in sense orientation.

Pdk-intron: Sequence of the second intron from the pyruvate orthophosphate dikinase gene (termed pdk gene) from Flayeria trinervia (Rosche & Westhoff (1995) Plant Molecular Biology 29-4: 663-678)

BN2-IND$^{antisense}$: A 261 by fragment from nucleotide +12 to +273 relative to the ATG startcodon of a *Brassica napus* homolog (homolog 2) of the *Arabidopsis thaliana* Ind1 gene, encoding a Basic Helix Loop Helix protein involved in pod dehiscence (corresponding to the nucleotide sequence of SEQ ID No 3 from the nucleotide at position 30 to the nucleotide at position 290). This fragment is cloned in antisense orientation.

3'ocs: the 3' untranslated end from the octopine synthase gene (De Greve et al. (1982) J. Mol. Appl. Genet. 1: 499-512; Gielen et al. (1984) EMBO J. 3: 835-846).

2. A chimeric bar gene comprising the following operably linked DNA fragments:

pSSuAra: a 1726 bp DNA fragment of promoter and leader sequence from the *Arabidopsis thaliana* rbcS ATS1A gene (Krebbers et al., 1988, Plant Mol. Biol. 11: 745-759).

bar: the coding sequence of the bialaphos resistance gene from *Streptomyces hygroscopicus* (Thompson et al., 1987, EMBO 6, 2519).

3'g7: A 211 bp DNA fragment containing the 3' end formation signals obtained from the 3' untranslated region of the TL-DNA gene 7 on pTiB6S3 (Dhaese et al., 1983, EMBO 2: 419; Velten and Schell, 1985, Nucl. Acids Res. 13: 6981).

PTCO212 is derived from pGVS1 (see above)

pTCO218 pTCO218 is a T-DNA vector comprising between the T-DNA borders

1. A dsRNA encoding chimeric gene (p35S-dsRNA/BN1-IND) comprising the following operably linked DNA fragments:

p35S: Promoter region from the Cauliflower Mosaic Virus 35S (Odell et al. (1985) Nature 313: 810-812).

BN1-IND$^{sense}$: A 269 by fragment from nucleotide +12 to +281 relative to the ATG startcodon of a *Brassica napus* homolog (homolog 1) of the *Arabidopsis thaliana* Ind1 gene, encoding a Basic Helix Loop Helix protein involved in pod dehiscence (corresponding to the nucleotide sequence of SEQ ID No 2 from the nucleotide at position 31 to the nucleotide at position 299). This fragment is cloned in sense orientation.

Pdk-intron: Sequence of the second intron from the pyruvate orthophosphate dikinase gene (termed pdk gene) from Flayeria trinervia (Rosche & Westhoff (1995) Plant Molecular Biology 29-4: 663-678)

BN1-IND$^{antisense}$: A 269 by fragment from nucleotide +12 to +281 relative to the ATG startcodon of a *Brassica napus* homolog (homolog 1) of the *Arabidopsis thaliana* Ind1 gene, encoding a Basic Helix Loop Helix protein involved in pod dehiscence (corresponding to the nucleotide sequence of SEQ ID No 2 from the nucleotide at position 31 to the nucleotide at position 299). This fragment is cloned in antisense orientation.

3'ocs: the 3' untranslated end from the octopine synthase gene (De Greve et al. (1982) J. Mol. Appl. Genet. 1: 499-512; Gielen et al. (1984) EMBO J. 3: 835-846).

2. A chimeric bar gene comprising the following operably linked DNA fragments:

pSSuAra: a 1726 bp DNA fragment of promoter and leader sequence from the *Arabidopsis thaliana* rbcS ATS1A gene (Krebbers et al., 1988, Plant Mol. Biol. 11: 745-759).

bar: the coding sequence of the bialaphos resistance gene from *Streptomyces hygroscopicus* (Thompson et al., 1987, EMBO 6, 2519).

3'g7: A 211 bp DNA fragment containing the 3' end formation signals obtained from the 3' untranslated region of the TL-DNA gene 7 on pTiB6S3 (Dhaese et al., 1983, EMBO 2: 419; Velten and Schell, 1985, Nucl. Acids Res. 13: 6981).

PTCO218 is derived from pGVS1 (see above)

Based on SHP1 (SHP2) gene sequences.

Two sequence regions, indicated AB and CD respectively from the SHP1 gene of *A. thaliana*, have been amplified by PCR and have been used to construct TDNA vectors containing chimeric dsRNA encoding genes capable of reducing the expression of SHP genes. The region indicated as "AB" has 100% sequence identity with SHP1 and about 88% sequence identity with SHP2, whereas the region indicated as "CD" has 100% sequence identity with SHP1 and about 77% sequence identity with SHP2.

pTCO233 pTCO233 is a T-DNA vector comprising between the T-DNA borders

1. A dsRNA encoding chimeric gene (p35S-dsRNA/At-SHP1$^{AB}$) comprising the following operably linked DNA fragments:

p35S: Promoter region from the Cauliflower Mosaic Virus 35S (Odell et al. (1985) Nature 313: 810-812).

At-SHP1/AB$^{sense}$: A fragment of the *Arabidopsis thaliana* SHP1 gene corresponding to the nucleotide sequence of SEQ ID No 9 from the nucleotide at position 258 to the nucleotide at position 375. This fragment is cloned in sense orientation.

Pdk-intron: Sequence of the second intron from the pyruvate orthophosphate dikinase gene (termed pdk gene) from Flayeria trinervia (Rosche & Westhoff (1995) Plant Molecular Biology 29-4: 663-678)

At-SHP1/AB$^{antisense}$: A fragment of the *Arabidopsis thaliana* SHP1 gene corresponding to the nucleotide sequence of SEQ ID No 9 from the nucleotide at position 258 to the nucleotide at position 375. This fragment is cloned in antisense orientation.

3'ocs: the 3' untranslated end from the octopine synthase gene (De Greve et al. (1982) J. Mol. Appl. Genet. 1: 499-512; Gielen et al. (1984) EMBO J. 3: 835-846).

2. A chimeric bar gene comprising the following operably linked DNA fragments:

pSSuAra: a 1726 bp DNA fragment of promoter and leader sequence from the *Arabidopsis thaliana* rbcS ATS1A gene (Krebbers et al., 1988, Plant Mol. Biol. 11: 745-759).

bar: the coding sequence of the bialaphos resistance gene from *Streptomyces hygroscopicus* (Thompson et al., 1987, EMBO 6, 2519).

3'g7: A 211 bp DNA fragment containing the 3' end formation signals obtained from the 3' untranslated region of the TL-DNA gene 7 on pTiB6S3 (Dhaese et al., 1983, EMBO 2: 419; Velten and Schell, 1985, Nucl. Acids Res. 13: 6981).

PTCO233 is derived from pGVS1 (see above).

pTCO234 pTCO234 is a T-DNA vector comprising between the T-DNA borders

1. A dsRNA encoding chimeric gene (p35S-dsRNA/At-SHP1$^{CD}$) comprising the following operably linked DNA fragments:

p35S: Promoter region from the Cauliflower Mosaic Virus 35S (Odell et al. (1985) Nature 313: 810-812).

At-SHP1/CD$^{sense}$: A fragment of the *Arabidopsis thaliana* SHP1 gene corresponding to the nucleotide sequence of SEQ ID No 9 from the nucleotide at position 567 to the nucleotide at position 726). This fragment is cloned in sense orientation.

Pdk-intron: Sequence of the second intron from the pyruvate orthophosphate dikinase gene (termed pdk gene) from Flayeria trinervia (Rosche & Westhoff (1995) Plant Molecular Biology 29-4: 663-678)

At-SHP1/CD$^{antisense}$: A fragment of the *Arabidopsis thaliana* SHP1 gene corresponding to the nucleotide sequence of SEQ ID No 9 from the nucleotide at position 567 to the nucleotide at position 726). This fragment is cloned in antisense orientation.

3'ocs: the 3' untranslated end from the octopine synthase gene (De Greve et al. (1982) J. Mol. Appl. Genet. 1: 499-512; Gielen et al. (1984) EMBO J. 3: 835-846).

2. A chimeric bar gene comprising the following operably linked DNA fragments:

pSSuAra: a 1726 bp DNA fragment of promoter and leader sequence from the *Arabidopsis thaliana* rbcS ATS1A gene (Krebbers et al., 1988, Plant Mol. Biol. 11: 745-759).

bar: the coding sequence of the bialaphos resistance gene from *Streptomyces hygroscopicus* (Thompson et al., 1987, EMBO 6, 2519).

3'g7: A 211 bp DNA fragment containing the 3' end formation signals obtained from the 3' untranslated region of the TL-DNA gene 7 on pTiB6S3 (Dhaese et al., 1983, EMBO 2: 419; Velten and Schell, 1985, Nucl. Acids Res. 13: 6981).

PTCO234 is derived from pGVS1 (see above).

The above T-DNA vectors were introduced into *Agrobacterium* pGV4000. This host strain is a rifampicin resistant derivative of C58, cured for pTiC58 (C58C1RifR) (Van Larebeke et al., 1974). The non-oncogenic acceptor Ti plasmid, pGV4000, is derived from the nopaline Ti plasmid pTiC58. The entire T-DNA region from pTiC58 has been substituted yielding pMP90 (Koncz and Schell, 1986). Plasmid pGV4000 has been derived from pMP90 by introducing a chloramphenicol resistance gene as described by Deblaere et al., 1985.

The resulting *Agrobacterium* strains were used to transform *Arabidopsis* plants according to the floral dipping method (Bechtold et al 1993., C. R. Acad. Sci. Paris, Sciences de la vie/Life Sciences, 316, 1194-1199) or *Brassica napus* plants according to the hypocotyl explant inoculation method (essentially as described in De Block et al, 1989, Plant Physiol., 91: 64 or in WO 00/04173). All *Brassica napus* transformations were performed using a doubled haploid line derived from N90-740.

Example 2

Analysis of Transgenic *Arabidopsis thaliana* Lines and *Brassica napus* Lines Comprising the Chimeric Genes of Example 1

A. Transgenic *Arabidopsis thaliana* Lines.

Transgenic *Arabidopsis thaliana* lines were obtained by transformation using all of the T-DNA vectors of Example 1. The obtained lines were analyzed for podshatter resistance. Pods from untransformed wt *Arabidopsis* lines open spontaneously at maturity. In contrast, each of the population of transgenic lines, transformed using particular T-DNA vectors, contained transgenic lines, the plants of which developed pods which did not open spontaneously at maturity (indicated herein as podshatter resistant). The fraction of transgenic lines with podshatter resistance in the total population of lines transformed using a particular T-DNA vector varied between 23% and 98% (see Table 1). The physical forces needed to open closed mature pods of the podshatter resistant transgenic lines were determined in a semi-quantitive way by applying pressure between two fingers. Pods which completely open along the dehiscence zone at the slightest pressure were classified as "+", whereas pods which open only at the base of the dehiscence zone, and need harder pressure to open completely were classified as "++". Pods which can only be crushed (and do not open along the dehiscence zone) were classified as "+++".

From the results summarized in Table 1, the following conclusions can be drawn.

Using a dsRNA chimeric gene with a strong promoter and a sense/antisense region which is completely homologous to the endogenous IND gene of *A. thaliana* (pTCO219)

a) virtually all transgenic lines develop pods which remain closed at maturity b) virtually all pods of these transgenic lines require considerable force to be opened.

Using a dsRNA chimeric gene with a relatively weak promoter and a sense/antisense region which is completely homologous to the endogenous IND gene of *A. thaliana* (pTKC89)

a) about 58% of transgenic lines develop pods which remain closed at maturity b) about half of the pods of these transgenic lines require only slight to moderate physical forces to be opened.

Using a dsRNA chimeric gene with a strong promoter and a sense/antisense region which has about 65% sequence identity to the endogenous IND gene of *A. thaliana* (pTCO212 and pTCO218)

a) only about one third of the transgenic lines develop pods which remain closed at maturity b) most of the pods of these transgenic lines require only slight to moderate physical forces to be opened.

Using a dsRNA chimeric gene with a strong promoter and a sense/antisense region which has about 100% sequence identity to the endogenous SHP1 gene of *A. thaliana* and about 71% or 88% sequence identity to the endogenous SHP2 gene of *A. thaliana* (pTCO233 and pTCO234)

a) only about one fourth to half of the transgenic lines develop pods which remain closed at maturity b) most of the pods of these transgenic lines require only slight (pTCO233) to moderate physical forces (pTCO234) to be opened.

From these results it can be concluded that moderate gene silencing using either a relatively weak promoter, or a sense/antisense region that exhibits lower than 88% and particularly around 65% sequence identity to a gene involved in dehiscence zone and valve margin development can be used to generate podshatter resistant *Arabidopsis thaliana* lines, all of the pods of which open along the dehiscence zone by application of only moderate physical forces.

TABLE 1

Podshatter resistance in transgenic *Arabidopsis* lines

| DsRNA chimeric gene | T-DNA vector | Sequence similarity to target | # transformants analyzed | Podshatter resistant | Podshatter resistance after aplying pressure | | |
|---|---|---|---|---|---|---|---|
| | | | | | +++ | ++ | + |
| 35S/AT-IND | PTCO219 | 100% | 203 | 199 (98%) | 199 | 0 | 0 |
| NOS/AT-IND | PTKC89 | 100% | 146 | 85 (58%) | 36 | 19 | 30 |
| 35S/BN1-IND | PTCO218 | 65% | 152 | 50 (33%) | 20 | 12 | 18 |
| 35S/BN2-IND | PTCO212 | 65% | 202 | 73 (36%) | 20 | 20 | 33 |
| 35S/AT-SHP$^{AB}$ | PTCO233 | 100-88% | 153 | 80 (52%) | 19 | 43 | 17 |
| 35S/AT-SHP$^{CD}$ | PTCO234 | 100-71% | 115 | 27 (23%) | 7 | 7 | 13 |

B. Transgenic *Brassica napus* Lines.

Transgenic *Brassica napus* lines were obtained by transformation using

T-DNA vectors pTCO212, pTCO218 and pTCO219 of Example 1. Lines with single copy T-DNA insertions were selected. These lines were analyzed for podshatter resistance. Pods from untransformed wt *B. napus* lines remain normally closed at maturity, but open upon application of relatively mildly forces. To determine podshatter resistance, a Random Impact Test (described above) was used to determine the half life of the pods (results summarized in Table 2 and FIG. 3).

Non-transgenic control lines have a pod half-life of about 10 s in the RIT.

Using a dsRNA chimeric gene with a strong promoter and a sense/antisense region which has about 90 to about 100% sequence identity to the endogenous *B. napus* IND genes homologous to the IND gene of *A. thaliana* (pTCO212 and pTCO218), the pods never opened along the dehiscence zone and were pulverized after a long time in the drum. No meaningful half-life could be determined.

Using a dsRNA chimeric gene with a strong promoter and a sense/antisense region which has about 65% sequence identity to the endogenous *B. napus* IND genes homologous to the IND gene of *A. thaliana* (pTCO219) pod half lives of about 15 to about 40 seconds in RIT were determined.

TABLE 2

Podshatter resistance in trangenic *B. napus* lines comprising the 35S-AT-IND chimeric gene (determined by RIT).

| Pod line | construct | Half life s | lld50 | uld50 | Corrected lower 95% | Corrected upper 95% |
| --- | --- | --- | --- | --- | --- | --- |
| Control | pTCO199 | 8.62 | 5.17 | 10.98 | 3.45 | 2.36 |
| Control | WT | 11.44 | 9.02 | 13.54 | 2.42 | 2.1 |
| Control | pTCO199 | 11.93 | 8.45 | 15.52 | 3.48 | 3.59 |
| Line 1 | pTCO219 | 15.97 | 12.44 | 22.68 | 3.53 | 6.71 |
| Line 2 | pTCO219 | 16.43 | 12.27 | 25.57 | 4.16 | 9.14 |
| Line 3 | pTCO219 | 16.54 | 14.43 | 19.05 | 2.11 | 2.51 |
| Line 4 | pTCO219 | 18.55 | 15.13 | 22.51 | 3.42 | 3.96 |
| Line 5 | pTCO219 | 20.5 | 15.13 | 28.58 | 5.37 | 8.08 |
| Line 6 | pTCO219 | 31.29 | 26.21 | 39.65 | 5.08 | 8.36 |
| Line 7 | pTCO219 | 32 | 25.63 | 44.98 | 6.37 | 12.98 |
| Line 8 | pTCO219 | 42.7 | 33.61 | 57.45 | 9.09 | 14.75 |

From these results it can be concluded that the methods according to the invention, as exemplified in *Arabidopsis thaliana*, yield similar results in oilseed rape crop plants.

The invention claimed is:

1. A method for reducing seed shattering in a plant of the species *Brassica napus, Brassica junceae* or *Brassica campestris* comprising the following steps:
 (1) creating a population of transgenic lines of said plant, wherein said transgenic lines of said population exhibit variation in podshatter resistance, and wherein said population is obtainable by
  (i) introducing a chimeric gene into cells of said plant, to create transgenic cells, said chimeric gene comprising the following operably linked DNA:
   (a) a plant-expressible promoter;
   (b) a DNA region which when transcribed yields a double-stranded RNA molecule comprising a first and second RNA region wherein
    said first RNA region comprises a nucleotide sequence of at least 200 consecutive nucleotides of the nucleotide sequence of SEQ ID NO: 1 other than a bHLH encoding region;
    said second RNA region comprises a nucleotide sequence complementary to said at least 200 consecutive nucleotides of said first RNA region;
    said first and second RNA regions are capable of base-pairing to form a double stranded RNA molecule between said at least 200 consecutive nucleotides of said first and second regions;
   (c) optionally, a 3' end region comprising transcription termination and polyadenylation signals functioning in cells of said plant;
    wherein said chimeric gene, when expressed in cells of said plant, increases podshatter resistance compared to podshatter resistance in an untransformed plant, while maintaining an agronomically relevant threshability of said pods of said plant;
  (ii) regenerating transgenic lines from said transgenic cells; and
 (2) selecting a podshatter resistant plant from said population wherein said plant has pods exhibiting reduced seed shattering while maintaining an agronomically relevant threshability of said pods.

2. The method of claim 1, wherein said plant expressible promoter is a CaMV 35S promoter.

3. The method of claim 1, wherein said first RNA region comprises a nucleotide sequence between position 27 and 239 of SEQ ID No 1.

4. The method of claim 1, wherein said agronomically relevant threshability corresponds to a half life time of the pods in a Random Impact test between 10 and 60 seconds.

5. The method of claim 4, wherein said agronomically relevant threshability corresponds to a half life time of the pods in a Random Impact test between 40 and 60 seconds.

6. A plant obtainable by the method of claim 1.

7. Seed from the plant of claim 6, said seed comprising a chimeric gene as described in claim 1.

8. The method of claim 1, wherein the plant is *Brassica napus*.

9. The method of claim 1, wherein the plant is *Brassica junceae*.

10. The method of claim 1, wherein the plant is *Brassica campestris*.

11. The method of claim 1, wherein the chimeric gene further comprises the following operably linked DNA:
 (c) a 3' end region comprising transcription termination and polyadenylation signals functioning in cells of said plant.

12. The method of claim 3, wherein the plant is *Brassica napus*.

13. The method of claim 4, wherein the plant is *Brassica napus*.

14. The method of claim 5, wherein the plant is *Brassica napus*.

* * * * *

SEQUENCE LISTING

<160> NUMBER OF SEQ ID NOS: 11

<210> SEQ ID NO 1
<211> LENGTH: 597
<212> TYPE: DNA
<213> ORGANISM: Artificial
<220> FEATURE:
<223> OTHER INFORMATION: nucleotide sequence of the INDEHISCENT gene of
      A. thaliana (AT-IND

<400> SEQUENCE: 1

```
atggaaaatg gtatgtataa aaagaaagga gtgtgcgact cttgtgtctc gtccaaaagc      60
agatccaacc acagccccaa aagaagcatg atggagcctc agcctcacca tctcctcatg     120
gattggaaca aagctaatga tcttctcaca caagaacacg cagcttttct caatgatcct     180
caccatctca tgttagatcc acctcccgaa accctaattc acttggacga agacgaagag     240
tacgatgaag acatggatgc gatgaaggag atgcagtaca tgatcgccgt catgcagccc     300
gtagacatcg accctgccac ggtccctaag ccgaaccgcc gtaacgtaag gataagcgac     360
gatcctcaga cggtggttgc tcgtcggcgt cgggaaagga tcagcgagaa gatccgaatt     420
ctcaagagga tcgtgcctgg tggtgcgaag atggacacag cttccatgct cgacgaagcc     480
atacgttaca ccaagttctt gaaacggcag gtgaggattc ttcagcctca ctctcagatt     540
ggagctccta tggctaaccc ctcttacctt tgttattacc acaactccca accctga        597
```

<210> SEQ ID NO 2
<211> LENGTH: 643
<212> TYPE: DNA
<213> ORGANISM: Artificial
<220> FEATURE:
<223> OTHER INFORMATION: Nucleotide sequence of a INDEHISCENT homologue
      from Brassica napus (BN1-IND

<400> SEQUENCE: 2

```
gaattcgccc ttcgcatgta taaaagaag ggtctatgcg tctctagtcc aaaaactcta       60
tatgtctggt tcaaaagcag atgcagcagc catagcccca atagtcatga tggagcctca     120
tcatctcctt atgaactgga acaaacctat tgatctcatt acacaagaaa actcttttaa     180
```

-continued

```
ccacaatcct catttcatgg tagatccacc ttccgaaacc ctaagccact tccagccccc      240
gccgacagtc ttctccgatc ccggaggagg agaggaagca gaagacgaag aaggagagga      300
agagatagat gagatgaagg agatgcaata cgcgattgct gccatgcagc ccgtagacat      360
cgatccagcc accgttccta agccgaaccg ccgtaacgta agggtaagcg aggacccca       420 gacggtggtg gctcgtcggc gtagagaaag gataagcgag aagatccgga tattgaagag      480
gatggtgcca ggcggtgcaa agatggacac tgcctccatg cttgacgaag ccatccgcta      540
caccaagttc ttgaaacggc aggtgaggct tcttcagcct cacactcagc ttggggctcc      600
tatgtctgac ccttctcgcc tttgttatta ccacaactct caa                       643
```

```
<210> SEQ ID NO 3
<211> LENGTH: 660
<212> TYPE: DNA
<213> ORGANISM: Artificial
<220> FEATURE:
<223> OTHER INFORMATION: nucleotide sequence of a second INDEHISCENT
      homologue from Brassica napus (BN2-IND

<400> SEQUENCE: 3
```

```
gaattcgccc ttggcatgta caagaagaaa ggtctatgcg tctctagtcc aaaaactcta      60
tatatgtctg gctcaaaagc agatgcagcc atagccccaa tagtcatgat ggagcatcat     120
catctcctta tgaattggaa caaacctatt gatctcatta cagaagaaaa ctctttaac     180 cacaatcctc atttcatgt agatccacct tccgaaaccc taagccactt ccagccccg      240 ccgacaatct tctccggtca cggaggagga gaggaagcag cagaagaaga agaagaagaa     300
ggagaggaag agatggatcc gatgaagaag atgcaatacg cgattgctgc catgcagccc     360
gtagacctcg atccagccac cgttcctaag ccgaaccgcc gtaacgtaag ggtaagcgac     420
gaccctcaga cggtggtggc tcgtcggcgt agagaaagga taagcgagaa gatccggata    480
ttgaggagga tggtgccagg cggtgcaaag atggacactg cctccatgct cgacgaagcc    540
atccgctaca ccaagttctt gaaacggcag gtgaggctag cttcttcagc ctcacactca    600
gcttggagct cctatgtctg acccttcttg cctttgttat tatcataact cgcagccctg    660
```

```
<210> SEQ ID NO 4
<211> LENGTH: 20
<212> TYPE: DNA
<213> ORGANISM: Artificial
<220> FEATURE:
<223> OTHER INFORMATION: common nucleotide sequence of oligonucleotides
      CO109/CO111

<400> SEQUENCE: 4
aggtctatgc gtctctagtc                                                  20
```

```
<210> SEQ ID NO 5
<211> LENGTH: 20
<212> TYPE: DNA
<213> ORGANISM: artificial
<220> FEATURE:
<223> OTHER INFORMATION: common nucleotide sequence of oligonucleotides
      CO110/CO112

<400> SEQUENCE: 5
tcttcttctg ctgcttcctc                                                  20
```

```
<210> SEQ ID NO 6
<211> LENGTH: 20
```

```
<212> TYPE: DNA
<213> ORGANISM: Artificial
<220> FEATURE:
<223> OTHER INFORMATION: common nucleotide sequence of oligonucleotides
      CO113/CO114

<400> SEQUENCE: 6
cctctccttc ttcgtcttct                                                    20

<210> SEQ ID NO 7
<211> LENGTH: 20
<212> TYPE: DNA
<213> ORGANISM: Artificial
<220> FEATURE:
<223> OTHER INFORMATION: common nucleotide sequence of oligonucleotides
      CO115/CO117

<400> SEQUENCE: 7
aggagtgtgc gactcttgtg                                                    20

<210> SEQ ID NO 8
<211> LENGTH: 19
<212> TYPE: DNA
<213> ORGANISM: Artificial
<220> FEATURE:
<223> OTHER INFORMATION: common nucleotide sequence of oligonucleotides
      CO116/CO118

<400> SEQUENCE: 8
tcttcgtctt cgtccaagt                                                     19

<210> SEQ ID NO 9
<211> LENGTH: 895
<212> TYPE: DNA
<213> ORGANISM: Artificial
<220> FEATURE:
<223> OTHER INFORMATION: nucleotide sequence of the SHATTERPROOF 1 gene
      of A. thaliana (AT-SHP1

<400> SEQUENCE: 9
ggatcaatgg aggaaggtgg gagtagtcac gacgcagaga gtagcaagaa actagggaga        60
gggaaaatag agataaagag gatagagaac acaacaaatc gtcaagttac tttctgcaaa       120
cgacgcaatg gtcttctcaa gaaagcttat gaactctctg tcttgtgtga tgccgaagtt       180
gccctcgtca tcttctccac tcgtggccgt ctctatgagt acgccaacaa cagtgtgagg       240
ggtacaattg aaaggtacaa gaaagcttgt tccgatgccg tcaaccctcc ttccgtcacc       300
gaagctaata ctcagtacta tcagcaagaa gcctctaagc ttcggaggca gattcgagat       360
attcagaatt caaataggca tattgttggg gaatcacttg gttccttgaa cttcaaggaa       420
ctcaaaaacc tagaaggacg tcttgaaaaa ggaatcagcc gtgtccgctc caaaagaat        480 gagctgttag tggcagagat agagtatatg cagaagaggg aaatggagtt gcaacacaat       540
aacatgtacc tgcgagcaaa gatagccgaa ggcgccagat tgaatccgga ccagcaggaa       600
tcgagtgtga tacaagggac gacagtttac gaatccggtg tatcttctca tgaccagtcg       660
cagcattata atcggaacta tattccggtg aaccttcttg aaccgaatca gcaattctcc       720
ggccaagacc aacctcctct tcaacttgtg taactcaaaa catgataact tgtttcttcc       780
cctcataacg attaagagag agacgagaga gttcatttta tatttataac gcgactgtgt       840
attcatagtt taggttctaa taatgataat aacaaaactg ttgtttcttt gcttc           895

<210> SEQ ID NO 10
```

```
<211> LENGTH: 963
<212> TYPE: DNA
<213> ORGANISM: Artificial
<220> FEATURE:
<223> OTHER INFORMATION: nucleotide sequence of the SHATTERPROOF 2 gene
      of A. thaliana (AT-SHP2

<400> SEQUENCE: 10
gaattcatct tcccatcctc acttctcttt ctttctgatc ataattaatc ttgctaagcc      60
agctagggct tatagaaatg gagggtggtg cgagtaatga agtagcagag agcagcaaga     120
agatagggag agggaagata gagataaaga ggatagagaa cactacgaat cgtcaagtca     180
ctttctgcaa acgacgcaat ggtttactca agaaagctta tgagctctct gtcttgtgtg     240
acgctgaggt tgctcttgtc atcttctcca ctcgaggccg tctctacgag tacgccaaca     300
acagtgtgag aggaacaata gaaaggtaca agaaagcttg ctccgacgcc gttaaccctc     360
cgaccatcac cgaagctaat actcagtact atcagcaaga ggcgtctaaa ctccggagac     420
agattcggga cattcagaat ttgaacagac acattcttgg tgaatctctt ggttccttga     480
actttaagga actcaagaac cttgaaagta ggcttgagaa aggaatcagt cgtgtccgat     540
ccaagaagca cgagatgtta gttgcagaga ttgaatacat gcaaaaaagg gaaatcgagc     600
tgcaaaacga taacatgtat ctccgctcca agattactga agaacaggt ctacagcaac      660 aagaatcgag tgtgatacat caagggacag tttacgagtc gggtgttact tcttctcacc     720
agtcggggca gtataaccgg aattatattg cggttaacct tcttgaaccg aatcagaatt     780
cctccaacca agaccaacca cctctgcaac ttgtttgatt cagtctaaca taagcttctt     840
tcctcagcct gagatcgatc tatagtgtca cctaaatgcg gccgcgtccc tcaacatcta     900
gtcgcaagct gaggggaacc actagtgtca tacgaacctc aagagacgg ttacacaaac      960 ggg                                                                   963

<210> SEQ ID NO 11
<211> LENGTH: 931
<212> TYPE: DNA
<213> ORGANISM: Artificial
<220> FEATURE:
<223> OTHER INFORMATION: nucleotide sequence of the ALCATRAZ gene of A.
      thaliana (AT-ALC)

<400> SEQUENCE: 11
agagagagag agagagagag agatgggtga ttctgacgtc ggtgatcgtc ttccccctcc      60
atcttcttcc gacgaactct cgagcttcct ccgacagatt ctttcccgta ctcctacagc     120
tcaaccttct tcaccaccga agagtactaa tgtttcctcc gctgagacct tcttcccttc     180
cgtttccggc ggagctgttt cttccgtcgg ttatggagtc tctgaaactg gccaagacaa     240
atatgctttc gaacacaaga gaagtggagc taaacagaga aattcgttga agagaaacat     300
tgatgctcaa ttccacaact tgtctgaaaa gaagaggagg agcaagatca acgagaaaat     360
gaaagctttg cagaaactca ttcccaattc aacaagact gataaagcct caatgcttga      420
tgaagctata gaatatctga agcagcttca acttcaagtc cagactttag ccgttatgaa     480
tggtttaggc ttaaacccta tgcgattacc acaggttcca cctccaactc atacaaggat     540
caatgagacc ttagagcaag acctgaacct agagactctt ctcgctgctc ctcactcgct     600
ggaaccagct aaaacaagtc aaggaatgtg cttttccaca gccactctgc tttgaagata     660
acattcagac aatgatgatg atcggaattc ctctagtacc tgccagacag gagtgaacaa     720
tgttttgagt tttagcattg gccagatttc tatgttcagt tatagttatg ctaataagct     780
```

```
ttaggagtga acaaaatctg agtagtttga ttataatgat gtctgaagca gattatatat        840
aaaagactaa tttacttaca tatgagatga ttattacaac tatcaaatga ctatgtctgt        900
gagttgcatc caaaaaaaaa aaaaaaaaaa a                                       931
```